(12) United States Patent
Taylor et al.

(10) Patent No.: US 8,795,325 B2
(45) Date of Patent: Aug. 5, 2014

(54) HANDLE ASSEMBLY FOR ARTICULATED ENDOSCOPIC INSTRUMENTS

(75) Inventors: Eric J. Taylor, Middletown, CT (US); Peter Hathaway, Lebanon, CT (US); Kevin Sniffin, Danbury, CT (US)

(73) Assignee: Covidien LP, Mansfield, MA (US)

( * ) Notice: Subject to any disclaimer, the term of this patent is extended or adjusted under 35 U.S.C. 154(b) by 1521 days.

(21) Appl. No.: 12/443,040

(22) PCT Filed: Oct. 4, 2007

(86) PCT No.: PCT/US2007/021480
§ 371 (c)(1), (2), (4) Date: Mar. 26, 2009

(87) PCT Pub. No.: WO2008/045374
PCT Pub. Date: Apr. 17, 2008

(65) Prior Publication Data
US 2010/0076260 A1    Mar. 25, 2010

Related U.S. Application Data

(60) Provisional application No. 60/849,560, filed on Oct. 5, 2006.

(51) Int. Cl.
*A61B 17/00* (2006.01)

(52) U.S. Cl.
USPC ...................................................... 606/205

(58) Field of Classification Search
USPC ................. 606/139, 169–174, 205, 206, 207; 227/175.1, 176, 178.1
See application file for complete search history.

(56) References Cited

U.S. PATENT DOCUMENTS

| | | | |
|---|---|---|---|
| 1,822,330 A | 9/1931 | Ainslie | |
| 2,327,353 A | 8/1943 | Karle | |
| 3,073,311 A | 1/1963 | Tibbs et al. | |
| 4,236,470 A | 12/1980 | Stenson | |
| 5,037,433 A | 8/1991 | Wilk et al. | |
| 5,042,707 A | 8/1991 | Taheri | |

(Continued)

FOREIGN PATENT DOCUMENTS

| | | |
|---|---|---|
| DE | 43 99 397 A1 | 7/1994 |
| WO | WO 99/15090 | 4/1999 |
| WO | WO 00/67834 A | 11/2000 |

OTHER PUBLICATIONS

International Search Report for PCT/US2007/021480 date of completion is Feb. 28, 2008 (2 pages).

(Continued)

*Primary Examiner* — Tuan V Nguyen (57) ABSTRACT

An endoscopic surgical instrument is provided and includes a handle assembly for operating the surgical instrument, an articulatable neck assembly supported on and extending from the handle assembly, and an end effector operatively supported on the neck assembly. The handle assembly includes a housing; a trigger operatively supported on the housing; at least one actuation shaft operatively connected to the trigger and extending from the housing, wherein an actuation of the trigger imparts axial translation to the actuation shaft; and at least one articulation cable operable from the housing. The end effector includes a pair of pivotably mounted, juxtaposed jaws, wherein the jaws are movable at least between an open position and a closed position, and wherein a distal end of an actuation shaft is operatively engaged with the pair of jaws to effectuate opening and closing of the jaws.

13 Claims, 12 Drawing Sheets

(56) References Cited

U.S. PATENT DOCUMENTS

| | | | |
|---|---|---|---|
| 5,100,430 A | 3/1992 | Avellanet et al. | |
| 5,209,747 A | 5/1993 | Knoepfler | |
| 5,300,082 A | 4/1994 | Sharpe et al. | |
| 5,308,353 A | 5/1994 | Beurrier | |
| 5,314,445 A | 5/1994 | Heidmueller née Degwitz et al. | |
| 5,330,502 A | 7/1994 | Hassler et al. | |
| 5,346,504 A * | 9/1994 | Ortiz et al. | 606/192 |
| 5,350,391 A | 9/1994 | Iacovelli | |
| 5,374,277 A | 12/1994 | Hassler | |
| 5,389,103 A | 2/1995 | Melzer et al. | |
| 5,403,342 A | 4/1995 | Tovey et al. | |
| 5,439,478 A | 8/1995 | Palmer | |
| 5,454,823 A | 10/1995 | Richardson et al. | |
| 5,454,827 A | 10/1995 | Aust et al. | |
| 5,480,406 A | 1/1996 | Nolan et al. | |
| 5,540,706 A | 7/1996 | Aust et al. | |
| 5,549,637 A | 8/1996 | Crainich | |
| 5,564,615 A | 10/1996 | Bishop et al. | |
| 5,575,799 A | 11/1996 | Bolanos et al. | |
| 5,582,617 A | 12/1996 | Klieman et al. | |
| 5,591,181 A | 1/1997 | Stone et al. | |
| 5,601,224 A | 2/1997 | Bishop et al. | |
| 5,620,415 A | 4/1997 | Lucey et al. | |
| 5,674,229 A | 10/1997 | Tovey et al. | |
| 5,690,652 A | 11/1997 | Wurster et al. | |
| 5,690,653 A | 11/1997 | Richardson et al. | |
| 5,704,534 A | 1/1998 | Huitema | |
| 5,752,973 A | 5/1998 | Kieturakis | |
| 5,759,188 A | 6/1998 | Yoon | |
| 5,766,196 A | 6/1998 | Griffiths | |
| 5,779,646 A | 7/1998 | Koblish et al. | |
| 5,792,165 A | 8/1998 | Klieman et al. | |
| 5,797,537 A | 8/1998 | Oberlin et al. | |
| 5,797,927 A | 8/1998 | Yoon | |
| 5,814,054 A | 9/1998 | Kortenbach et al. | |
| 5,817,119 A | 10/1998 | Klieman et al. | |
| 5,827,323 A | 10/1998 | Klieman et al. | |
| 5,876,412 A | 3/1999 | Piraka | |
| 5,897,563 A | 4/1999 | Yoon et al. | |
| 5,906,630 A | 5/1999 | Anderhub et al. | |
| 5,928,136 A | 7/1999 | Barry | |
| 5,954,731 A | 9/1999 | Yoon | |
| 5,954,733 A | 9/1999 | Yoon | |
| 5,957,937 A | 9/1999 | Yoon | |
| 5,984,932 A | 11/1999 | Yoon | |
| 5,993,466 A | 11/1999 | Yoon | |
| 5,993,467 A | 11/1999 | Yoon | |
| 5,997,565 A | 12/1999 | Inoue | |
| 6,004,332 A | 12/1999 | Yoon et al. | |
| 6,017,358 A | 1/2000 | Yoon et al. | |
| 6,027,522 A | 2/2000 | Palmer | |
| 6,077,287 A | 6/2000 | Taylor et al. | |
| 6,080,180 A | 6/2000 | Yoon | |
| 6,086,601 A | 7/2000 | Yoon | |
| 6,126,665 A | 10/2000 | Yoon | |
| 6,139,563 A | 10/2000 | Cosgrove, III et al. | |
| 6,143,005 A | 11/2000 | Yoon et al. | |
| 6,171,316 B1 | 1/2001 | Kovac et al. | |
| 6,206,893 B1 | 3/2001 | Klein et al. | |
| 6,214,028 B1 | 4/2001 | Yoon et al. | |
| 6,223,100 B1 | 4/2001 | Green | |
| 6,224,614 B1 | 5/2001 | Yoon | |
| 6,261,307 B1 | 7/2001 | Yoon et al. | |
| 6,319,262 B1 | 11/2001 | Bates et al. | |
| 6,358,259 B1 | 3/2002 | Swain et al. | |
| 6,494,888 B1 | 12/2002 | Laufer et al. | |
| 6,506,196 B1 | 1/2003 | Laufer | |
| 6,517,539 B1 | 2/2003 | Smith et al. | |
| 6,569,105 B1 | 5/2003 | Kortenbach et al. | |
| 6,582,450 B2 | 6/2003 | Ouchi | |
| 6,638,287 B2 | 10/2003 | Danitz et al. | |
| 6,663,639 B1 | 12/2003 | Laufer et al. | |
| 6,663,641 B1 | 12/2003 | Kovac et al. | |
| 6,666,854 B1 | 12/2003 | Lange | |
| 6,676,676 B2 | 1/2004 | Danitz et al. | |
| 6,743,239 B1 | 6/2004 | Kuehn et al. | |
| 6,743,240 B2 | 6/2004 | Smith et al. | |
| 6,755,843 B2 | 6/2004 | Chung et al. | |
| 6,773,441 B1 | 8/2004 | Laufer et al. | |
| 6,821,285 B2 | 11/2004 | Laufer et al. | |
| 6,835,200 B2 | 12/2004 | Laufer et al. | |
| 6,889,116 B2 | 5/2005 | Jinno | |
| 6,936,061 B2 | 8/2005 | Sasaki | |
| 6,972,017 B2 | 12/2005 | Smith et al. | |
| 6,981,628 B2 | 1/2006 | Wales | |
| 6,997,931 B2 | 2/2006 | Sauer et al. | |
| 7,052,489 B2 | 5/2006 | Griego et al. | |
| 7,063,715 B2 | 6/2006 | Onuki et al. | |
| 7,107,124 B2 | 9/2006 | Green | |
| 7,153,314 B2 | 12/2006 | Laufer et al. | |
| 7,248,944 B2 | 7/2007 | Green | |
| 7,278,563 B1 | 10/2007 | Green | |
| 2001/0030219 A1 | 10/2001 | Green et al. | |
| 2006/0022014 A1 | 2/2006 | Shelton, IV et al. | |
| 2006/0069396 A1 | 3/2006 | Meade et al. | |
| 2006/0190034 A1 | 8/2006 | Nishizawa et al. | |
| 2006/0253126 A1 | 11/2006 | Bjerken et al. | |
| 2006/0282093 A1 | 12/2006 | Shelton, IV et al. | |
| 2007/0276430 A1 * | 11/2007 | Lee et al. | 606/205 |

OTHER PUBLICATIONS

European Search Report from European Patent Application No. 08 25 3237.

* cited by examiner

HANDLE ASSEMBLY FOR ARTICULATED ENDOSCOPIC INSTRUMENTS

CROSS-REFERENCE TO RELATED APPLICATIONS

This application is a National Stage Application of PCT/US2007/021480 filed Oct. 4, 2007 under 35USC §371 (a), which claims benefit of and priority to U.S. Provisional Patent Application Ser. No. 60/849,560 filed Oct. 5, 2006 the disclosures of each of the above-identified applications are hereby incorporated by reference in their entirety.

BACKGROUND

1. Technical Field

The present disclosure relates to systems and devices for manipulating and/or operating surgical instruments and, more particularly, to handle assemblies and devices for manipulating and/or operating open, endoscopic, endoluminal, and/or transluminal surgical instruments including surgical graspers, suturing devices, and/or stitching devices.

2. Background

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

One of the truly great advances in recent years to reduce the invasiveness of surgical procedures is endoscopic surgery. Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions. Also, the reduction in trauma to the abdominal wall and the physiology of the pneumoperitoneum has a positive impact on patients undergoing abdominal operations.

In continuing efforts to reduce the trauma of surgery, interest has recently developed in the possibilities of performing procedures to diagnose and surgically treat a medical condition without any incision in the abdominal wall by using a natural orifice (e.g., the mouth or anus) to access the target tissue. Such procedures are sometimes referred to as endoluminal procedures or natural orifice transluminal endoscopic surgery ("NOTES"). Although many such endoluminal procedures are still being developed, they generally utilize a flexible endoscope instrument or flexible catheter to provide access to the tissue target tissue. Endoluminal procedures have been used to treat conditions within the lumen including for example, treatment of gastroesophageal reflux disease in the esophagus and removal of polyps from the colon. In some instances, physicians have gone beyond the luminal confines of the gastrointestinal tract to perform intra-abdominal procedures. For example, using flexible endoscopic instrumentation, the wall of the stomach can be punctured and an endoscope advanced into the peritoneal cavity to perform various procedures. Using such endoluminal techniques, diagnostic exploration, liver biopsy, cholecystectomy, splenectomy, and tubal ligation have reportedly been performed in animal models. After the intra-abdominal intervention is completed, the endoscopic instrumentation is retracted into the stomach and the puncture closed. Other natural orifices, such as the anus or vagina, may also allow access to the peritoneal cavity.

In many surgical procedures, it is often necessary to suture bodily organs or tissue. Traditionally, suturing was accomplished by hand. Suturing during endoscopic surgery is especially challenging because of the small openings through which the suturing of bodily organs or tissues must be accomplished. Similarly, in endoluminal procedures for example, the site where sutures are to be applied may be deep in a lumen having a tortuous anatomy relatively distant from the access orifice (e.g., mouth or anus).

As with suturing, manipulation of tissue, sutures, needles and other materials is greatly complicated in endoscopic and endoluminal procedures because of the method of access to the operative site.

There is a need, however, for handle assemblies and the like configured and adapted to operate, manipulate and/or control surgical instruments, including open, endoscopic, endoluminal, and/or transluminal suturing devices, graspers, and the like.

SUMMARY

The present disclosure relates to handle assemblies and devices for manipulating and/or operating surgical instruments including endoscopic and endoluminal surgical suturing and/or stitching devices.

According to an aspect of the present disclosure, a handle assembly for operating a surgical instrument includes a housing; a trigger operatively supported on the housing; at least one actuation shaft operatively connected to the trigger and extending from the housing, wherein an actuation of the trigger imparts axial translation to the actuation shaft; and at least one articulation cable operable from the housing, each articulation cable including a distal end operatively connectable with an end effector and a proximal end operatively connected to an articulation control element supported on the housing.

In use, movement of the control element may result in movement of the at least one articulation cable. Movement of the at least one articulation cable in a first direction may cause an articulation of the end effector in a first direction and movement of the at least one articulation cable in a second direction may result in articulation of the end effector in a second direction. The control element may be selected from the group consisting of a slider, a dial, and a lever.

The handle assembly may further include a pair of articulation cables each having a proximal end operatively connected to the control element such that movement of the control element in a first direction results in movement of a first articulation cable in a first direction and movement of a second articulation cable in a second direction; and movement of the control element in a second direction may result in movement of the first articulation cable in the second direction and movement of the second articulation cable in the first direction.

The trigger may impart proximal axial movement to the actuation shaft when the trigger is squeezed, and distal axial movement to the actuation shaft when the trigger is released. The handle assembly may further include a ratchet mechanism operatively associated with the trigger, wherein the ratchet mechanism is configured to selectively maintain the position of the trigger relative to the housing. The handle assembly may further include a release assembly operatively associated with the ratchet mechanism, wherein the release assembly is configured such that actuation of the release assembly results in a disengagement of the ratchet mechanism. The ratchet mechanism may include a ratchet rack having a first end coupled to the trigger and a second end extending into the handle, and a pawl selectively operatively engageable with teeth of the ratchet rack. The release assembly may include a release button supported on the housing, and a release lever interconnecting the release button and the pawl, wherein actuation of the release button selectively engages and disengages the pawl and the ratchet rack. The pawl may be biased into engagement with the ratchet rack.

The handle assembly may further include a ratchet mechanism operatively associated with the articulation control element. The ratchet mechanism may be configured to selectively maintain the position of the articulation control element relative to the housing.

The ratchet mechanism may include a ratchet rack supported on the housing and operatively associated with the articulation control element and an articulation trigger supported on the articulation control element and operatively associated with the ratchet rack. The articulation trigger may be configured to maintain the relative position of the articulation control element. The articulation trigger may be incrementally movable along the ratchet rack.

According to a further aspect of the present disclosure, an endoscopic surgical instrument is provided and includes a handle assembly for operating the surgical instrument, an articulatable neck assembly supported on and extending from the handle assembly, wherein each actuation shaft and articulation cable extends through the neck assembly, and an end effector operatively supported on the neck assembly. The handle assembly includes a housing; a trigger operatively supported on the housing; at least one actuation shaft operatively connected to the trigger and extending from the housing, wherein an actuation of the trigger imparts axial translation to the actuation shaft; and at least one articulation cable operable from the housing, each articulation cable including a distal end operatively connectable with an end effector and a proximal end operatively connected to an articulation control element supported on the housing. The end effector includes a pair of pivotably mounted, juxtaposed jaws, wherein the jaws are movable at least between an open position and a closed position, and wherein a distal end of an actuation shaft is operatively engaged with the pair of jaws to effectuate opening and closing of the jaws.

In use, movement of the articulation control element may result in movement of the at least one articulation cable to effectuate an articulation of the neck assembly. Also, in use, movement of the at least one articulation cable in a first direction may cause an articulation of the end effector in a first direction and movement of the at least one articulation cable in a second direction may result in articulation of the end effector in a second direction.

The endoscopic surgical instrument may further include a pair of articulation cables each having a proximal end operatively connected to the articulation control element such that movement of the articulation control element in a first direction results in movement of a first articulation cable in a first direction and movement of a second articulation cable in a second direction; and movement of the control element in a second direction results in movement of the first articulation cable in the second direction and movement of the second articulation cable in the first direction.

The trigger may impart proximal axial movement to the actuation shaft when the trigger is squeezed to close the jaws, and distal axial movement to the actuation shaft when the trigger is released to open the jaws.

The handle assembly may further include a ratchet mechanism operatively associated with the trigger. The ratchet mechanism may be configured to selectively maintain the position of the trigger relative to the housing and thus the relative open or closed position of the jaws. The housing assembly may further include a release assembly operatively associated with the ratchet mechanism, wherein the release assembly may be configured such that actuation of the release assembly may result in a disengagement of the ratchet mechanism.

The ratchet mechanism may include a ratchet rack having a first end coupled to the trigger and a second end extending into the handle, and a pawl selectively operatively engageable with teeth of the ratchet rack. The release assembly may include a release button supported on the housing, and a release lever interconnecting the release button and the pawl, wherein actuation of the release button may selectively engage and disengage the pawl and the ratchet rack. The pawl may be biased into engagement with the ratchet rack.

The handle assembly may further include a ratchet mechanism operatively associated with the articulation control element. The ratchet mechanism may be configured to selectively maintain the position of the articulation control element relative to the housing to thereby maintain the relative articulation of the neck assembly. The ratchet mechanism may include a ratchet rack supported on the housing and operatively associated with the articulation control element and an articulation trigger supported on the articulation control element and operatively associated with the ratchet rack. The articulation trigger may be configured to maintain the relative position of the articulation control element.

The articulation trigger may be incrementally movable along the ratchet rack.

The pair of jaws may define a surgical grasper.

DETAILED DESCRIPTION OF THE DRAWINGS

The foregoing objects, features and advantages of the disclosure will become more apparent from a reading of the following description in connection with the accompanying drawings, in which.

DETAILED DESCRIPTION OF EMBODIMENTS

In the drawings and in the description which follow, the term "proximal", as is traditional, will refer to the end of the device which is closest to the operator, while the term "distal" will refer to the end of the device which is furthest from the operator.

Figure 1:
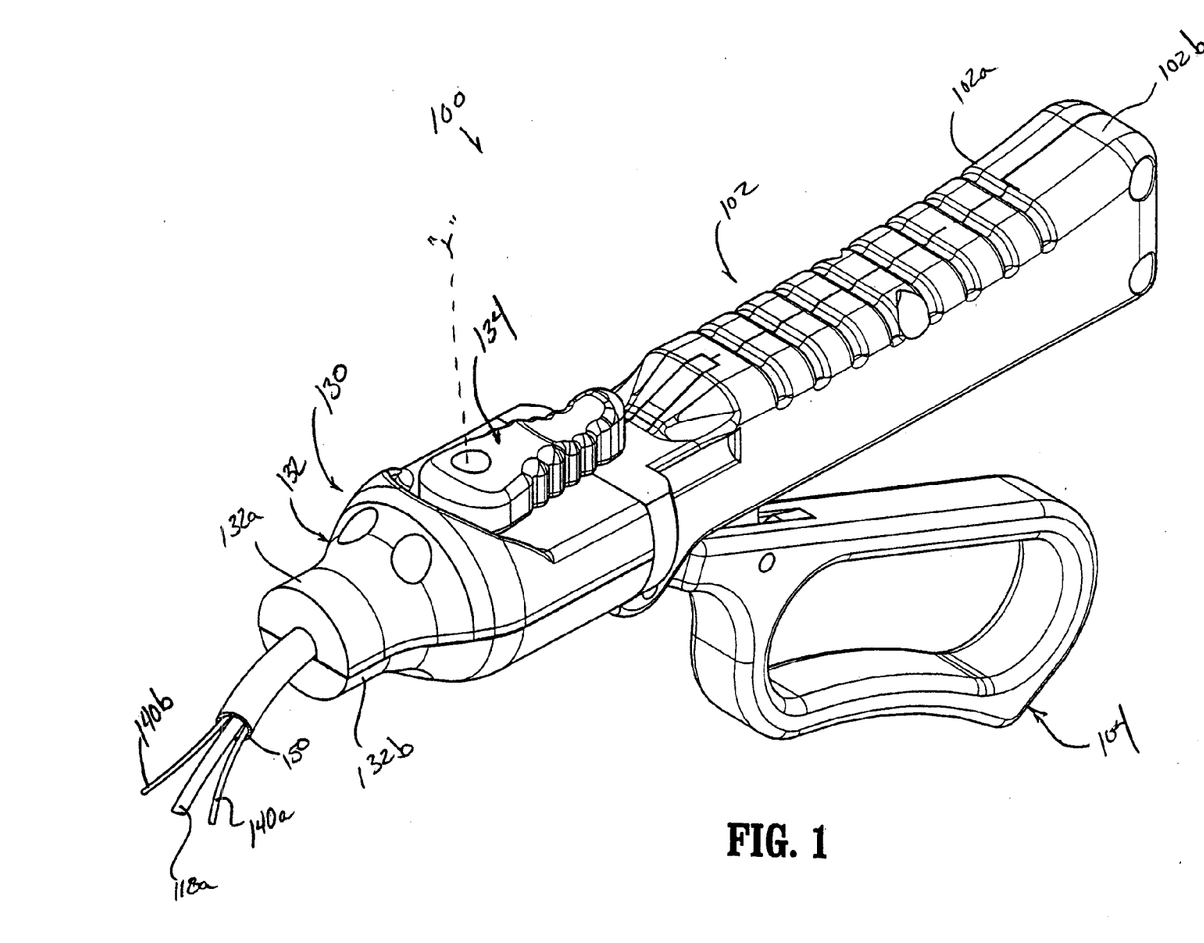
FIG. 1 is a perspective view of a handle assembly according to an embodiment of the present disclosure.
Figure 2:
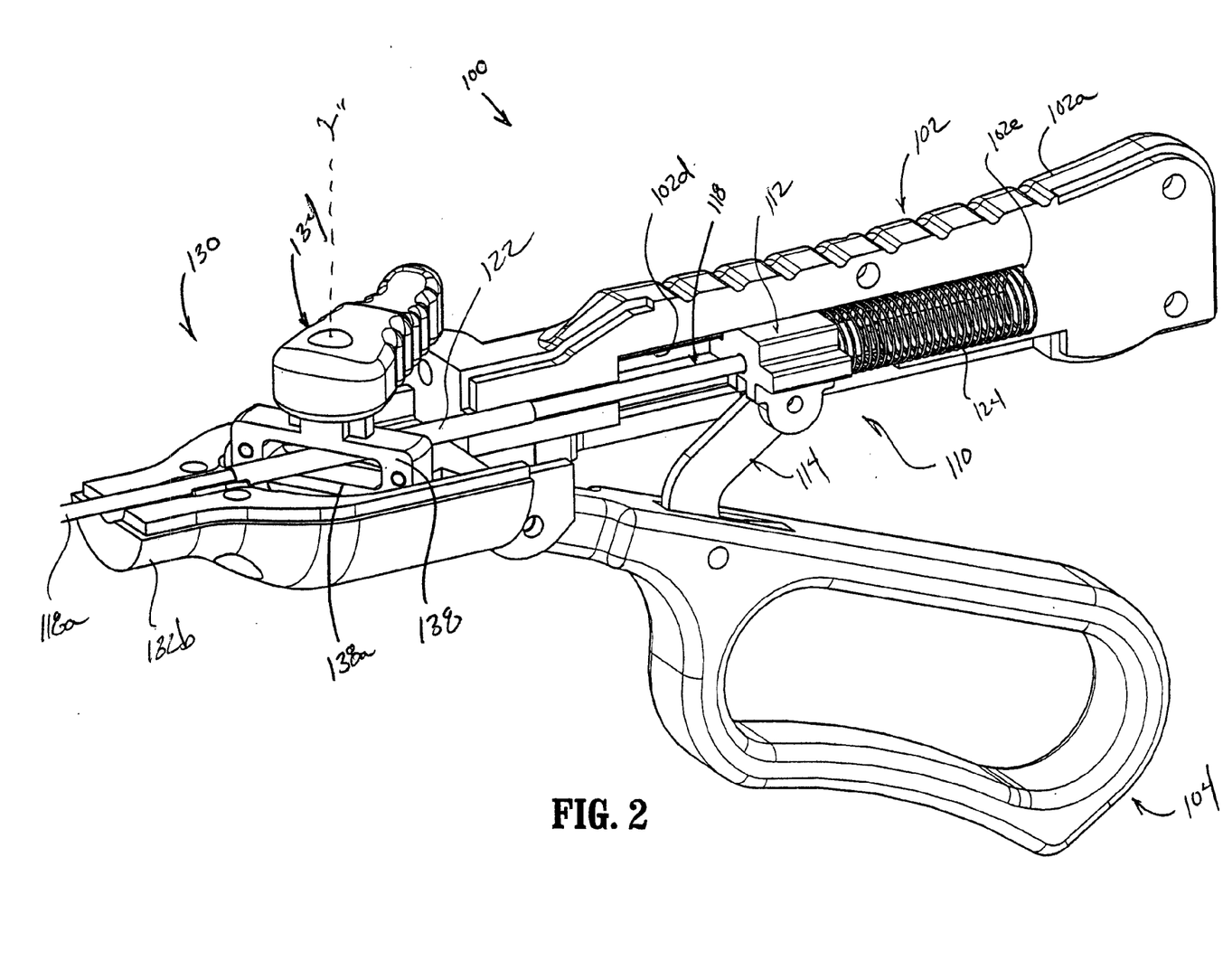
FIG. 2 is a perspective view of the handle assembly of FIG. 1 which a half-section of the fixed handle and a half-section of the articulation body removed therefrom.
Figure 3:
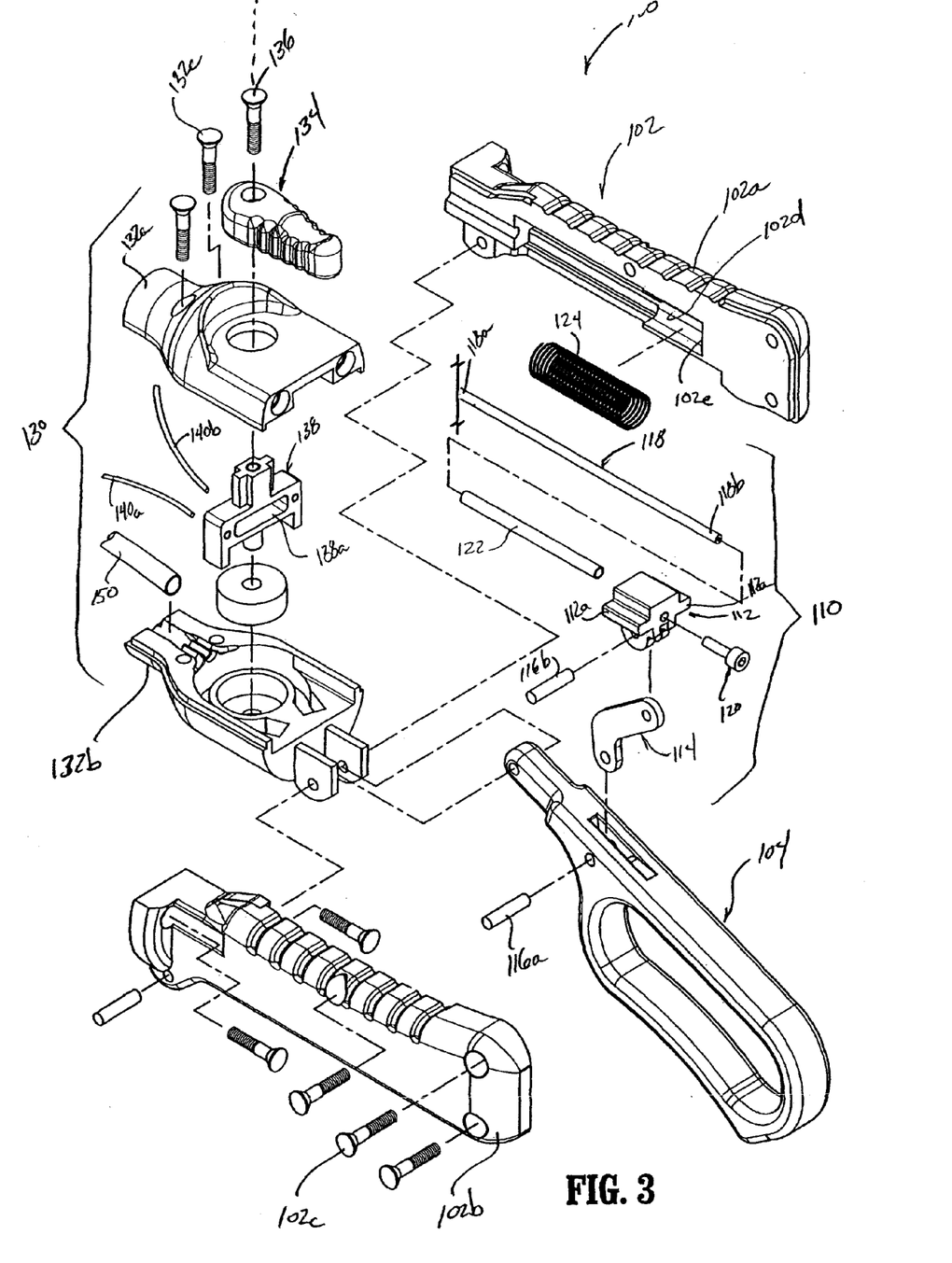
FIG. 3 is an exploded perspective view of the handle assembly of FIGS. 1 and 2.
Figure 4:
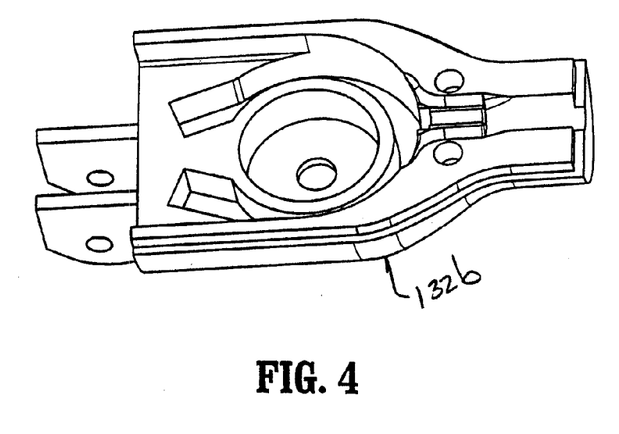
FIG. 4 is a perspective view of a half-section of the articulation body of FIGS. 1-3.

Referring initially to FIGS. 1-5, a handle assembly for operating, manipulating and/or controlling endoscopic and/or endoluminal devices and/or instruments, in accordance with an embodiment of the present disclosure, is generally designated as 100. Handle assembly 100 includes a housing 102, and an articulation assembly 130 supported on or otherwise operatively connected to a distal end of housing 102. Housing 102 includes a right-half section 102a and a left-half section 102b joinable to one another by suitable fastening elements 102c, such as screws 102c, as shown in FIG. 3.

Handle assembly 100 includes a trigger 104 operatively supported in and/or pivotally connected to housing 102 and extending therefrom. As will be described in greater detail below, trigger 104 is movable between a first un-actuated position, as seen in FIGS. 1 and 2, and a second actuated position, as seen in FIG. 7. In use, movement of trigger 104 between the first and second positions results in actuation and/or operation of an end effector (not shown). Trigger 104 is operatively associated or otherwise connected to an actuation mechanism 110 (see FIG. 6) of handle assembly 100.

Figure 5:
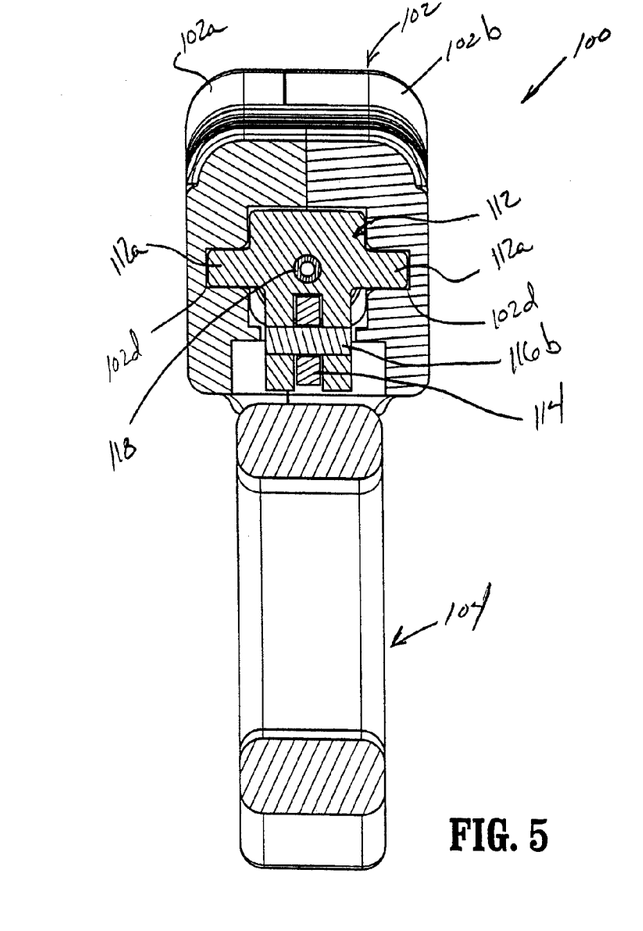
FIG. 5 is a cross-sectional view of the handle assembly of FIGS. 1-3, as taken through 5-5 of FIG. 7.

As seen in FIGS. 2, 3 and 5, actuation mechanism 110 includes an actuation block 112 slidably supported in juxtaposed channels 120d formed in half-sections sections 102a, 102b of housing 102. Actuation block 112 includes a pair of opposed tabs 112a extending therefrom for operative slidable engagement in channels 120d of half-sections 102a, 102b of housing 102.

Actuation mechanism 110 further includes an actuation link 114 pivotally inter-connected between trigger 104 and actuation block 112 via respective pins 116a, 116b. In operation, as will be described in greater detail below, as trigger 104 is approximated toward housing 102, actuation block 112 is axially moved in a first direction, and as trigger 104 is moved away from housing 102, actuation block 112 is axially moved in a second direction, opposite the first direction.

Actuation mechanism 110 includes an actuation rod or shaft 118 secured to actuation block 112 and extending from a distal end thereof. In one embodiment, actuation rod or shaft 118 may be flexible. A distal end 118a of actuation shaft 118 extends from handle assembly 100 and operatively engages an end effector (not shown), and a proximal end 118b of actuation shaft 118 operatively engages an adjustment screw 120. Adjustment screw 120 is configured and adapted to vary and/or adjust a length of actuation shaft 118.

A guide tube 122 is supported in housing 102 and extends distally therefrom and through articulation assembly 130. Actuation shaft 118 slidably extends through guide tube 122 while passing through articulation assembly 130.

Actuation mechanism 110 includes a suitable biasing member 124 interposed between actuation block 112 and a distal-facing surface 102e defined in housing 102.

As discussed above and as seen in FIGS. 1-4, 6 and 7, handle assembly 100 includes an articulation assembly 130 supported on or otherwise operatively connected to a distal end of housing 102. Articulation assembly 130 includes a housing 132 having a top-half section 132a and a bottom-half section 132b joinable to one another by suitable fastening elements 132c, such as screws 132c, as shown in FIG. 3. Articulation assembly 130 includes a lever, dial or other suitable structure 134 pivotably supported on housing 132 via a pin or screw 136. Pin 136 defines a pivot axis "Y" for lever 134.

Articulation assembly 130 includes a pivotable body, articulating member or other suitable body 138 pivotably supported in housing 132. Articulating member 138 is keyed to or otherwise operatively secured to lever 134 about a pivot axis that is common with the pivot axis of lever 134. Articulating member 138 defines a central lumen, opening or window 138a formed therein through which actuation shaft 118 passes.

Articulation assembly 130 further includes a pair of articulation cables 140a, 140b secured to opposite ends of articulation member 138. Each articulation cable 140a, 140b is secured to articulation member 138 at a location spaced a distance from the pivot axis thereof. In this manner, as will be described in greater detail below, rotation or pivoting of articulation member 138 about the pivot axis with cause one of the pair of articulation cables 140a, 140b to move in a first direction while the other of the pair of articulation cables 140a, 140b moves in a second direction, opposite to the first direction, and vice-versa. In this manner, articulation member 138 operates substantially as a see-saw. In use, movement of lever 134 results in articulation and/or operation of an end effector (not shown).

Handle assembly 100 may include an elongate sheath 150 extending over actuation shaft 118 and articulation cables 140a, 140b. A proximal end of sheath 150 may be secured to housing 132 of articulation assembly 130.

Sheath 150 may be fabricated from a flexible, non-radially expandable material. Sheath 150 may be rotationally rigid such that rotational force on handle assembly 100 transfers rotational force to the end effector. Sheath 150 functions to ensure that articulation cables 140a, 140b solely translate in an axial direction and do not deflect radially outward. Each articulation cable 140a, 140b and actuation shaft 118 may be fabricated from a suitable material, i.e., stainless steel, capable of transmitting axial and torsional forces.

With continued reference to FIGS. 1-7, a method of using and/or operating handle assembly 100 is shown and described. As seen in FIG. 2, when trigger 104 is in a first or un-actuated position, actuation block 112 is positioned proximate a distal end of channels 102*d* of housing 102.

As seen in FIG. 7, when trigger 104 is squeezed to a second or fully actuated position, actuation link 114 is moved proximally, as indicated by arrow "A" which, in turn, moves actuation block 112 proximally through channels 102*d* of housing 102. As actuation block 112 is moved proximally, actuation block 112 pulls actuation shaft 118 in a proximal direction, indicated arrow "A", and compresses biasing member 124 against distal-facing surface 102*e* of housing 102.

Movement of actuation shaft 118, in the direction of arrow "A", may result in a first operation or movement of an end effector (not shown), such as, for example, an approximation or an opening of jaws of the end effector.

Figure 6:
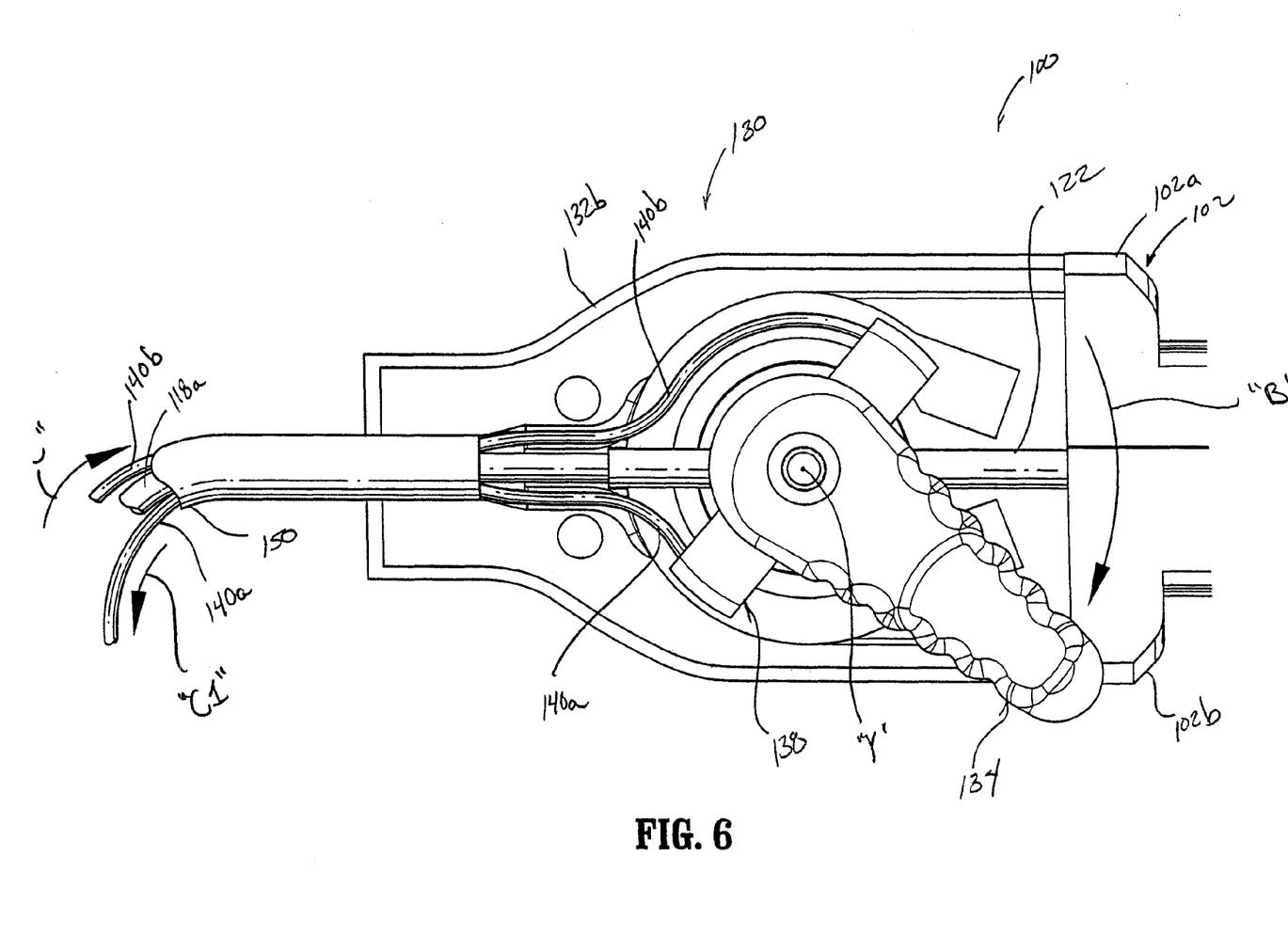
FIG. 6 is a top plan view of an articulation assembly of the handle assembly of FIGS. 1-3, illustrating an operation thereof.
Figure 7:
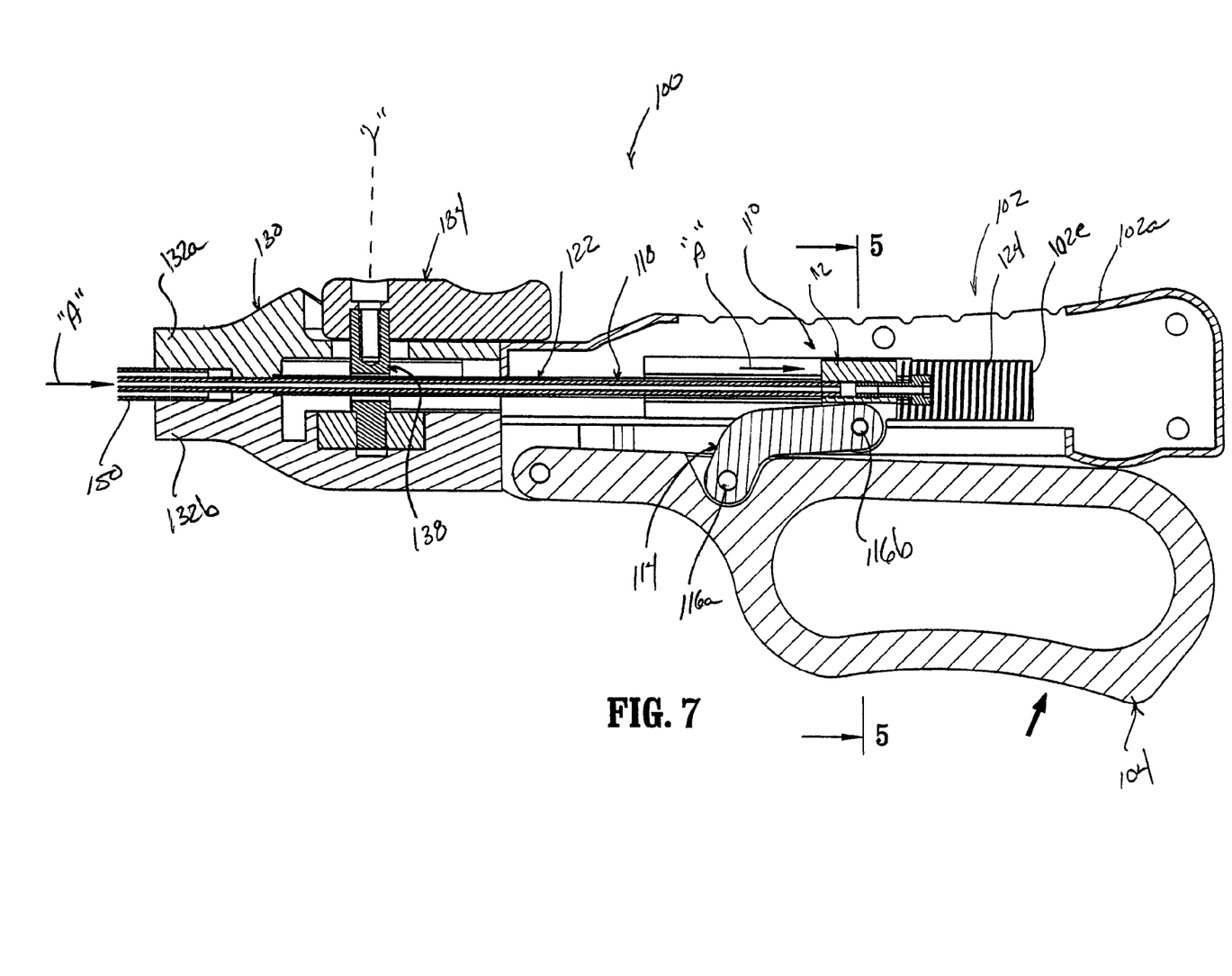
FIG. 7 is a longitudinal, cross-sectional view of the handle assembly of FIGS. 1-3, illustrating an operation thereof.

Additionally, as seen in FIG. 6, as lever 134 is pivoted in a first direction about pivot axis "Y", as indicated by arrow "B", articulation member 138 is also pivoted about pivot axis "Y" in the direction of arrow "B". As articulation member 138 is pivoted in the direction of arrow "B", articulation cable 140*b* is withdrawn in a proximal direction, as indicated by arrow "C", and articulation cable 140*a* is simultaneously moved in a distal direction, as indicated by arrow "C1". It is understood that, as articulation member 138 is pivoted in the direction opposite of arrow "B", articulation cable 140*b* is moved in a distal direction and articulation cable 140*a* is simultaneously moved in a proximal direction. Pivoting or movement of lever 134 thus may impart an operation or movement in an end effector (not shown).

Figure 8:
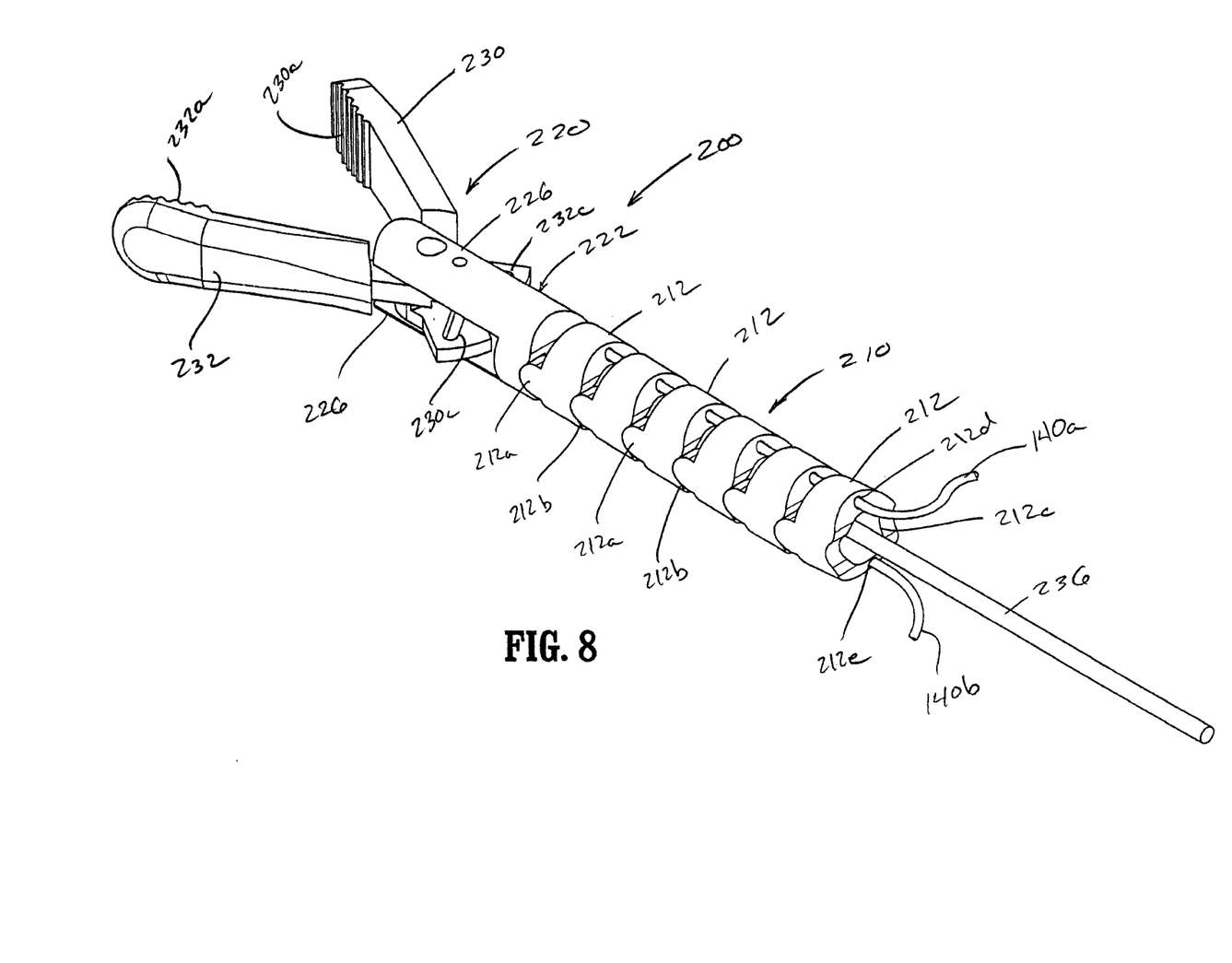
FIG. 8 is a rear perspective view of an end effector for use with the handle assembly of FIGS. 1-7.
Figure 9:
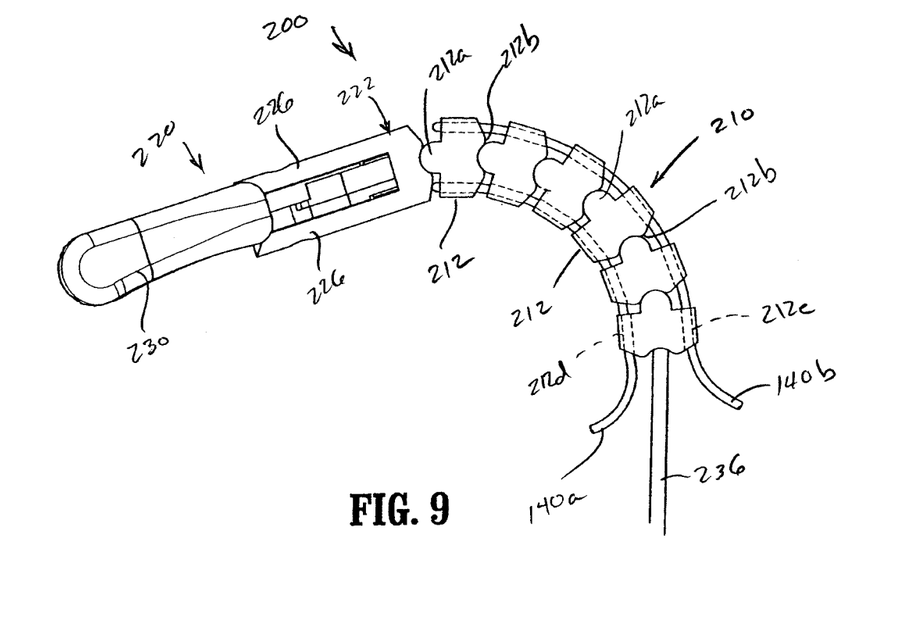
FIG. 9 is a top plan view of view of the end effector of FIG. 8, illustrating the end effector articulated in a first direction.
Figure 10:
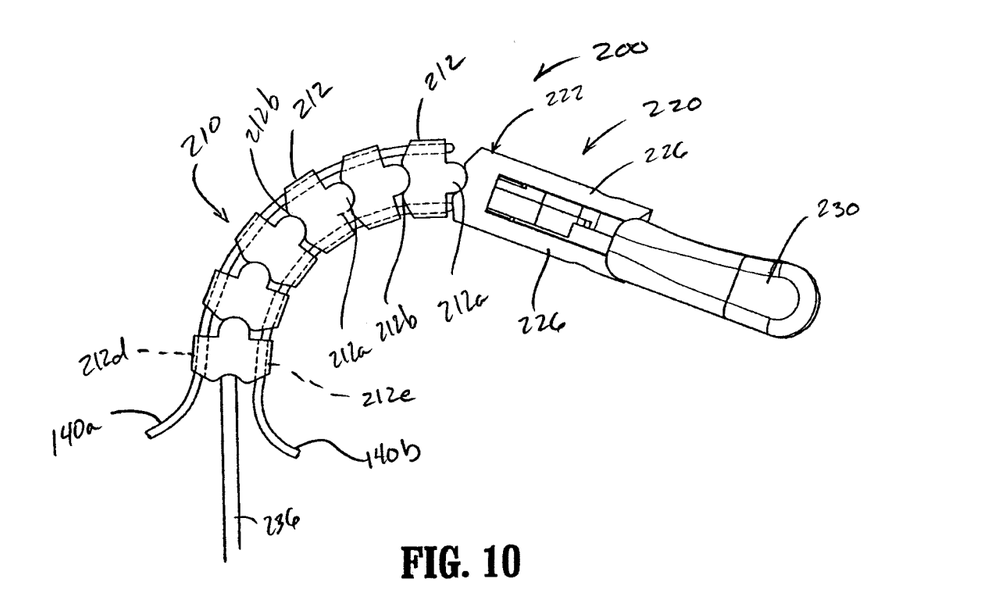
FIG. 10 is a top plan view of view of the end effector of FIG. 8, illustrating the end effector articulated in a second direction.
Figure 11:
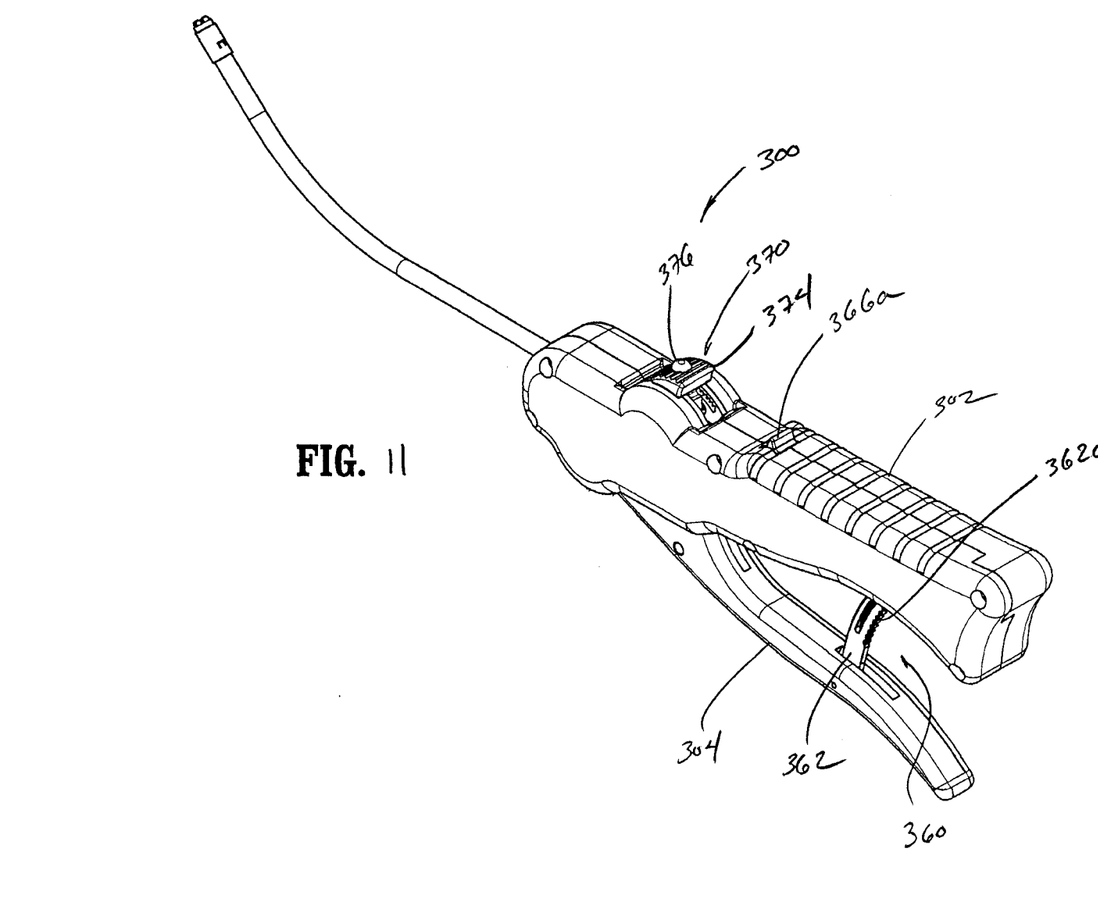
FIG. 11 is a perspective view of a handle assembly according to another embodiment of the present disclosure.
Figure 12:
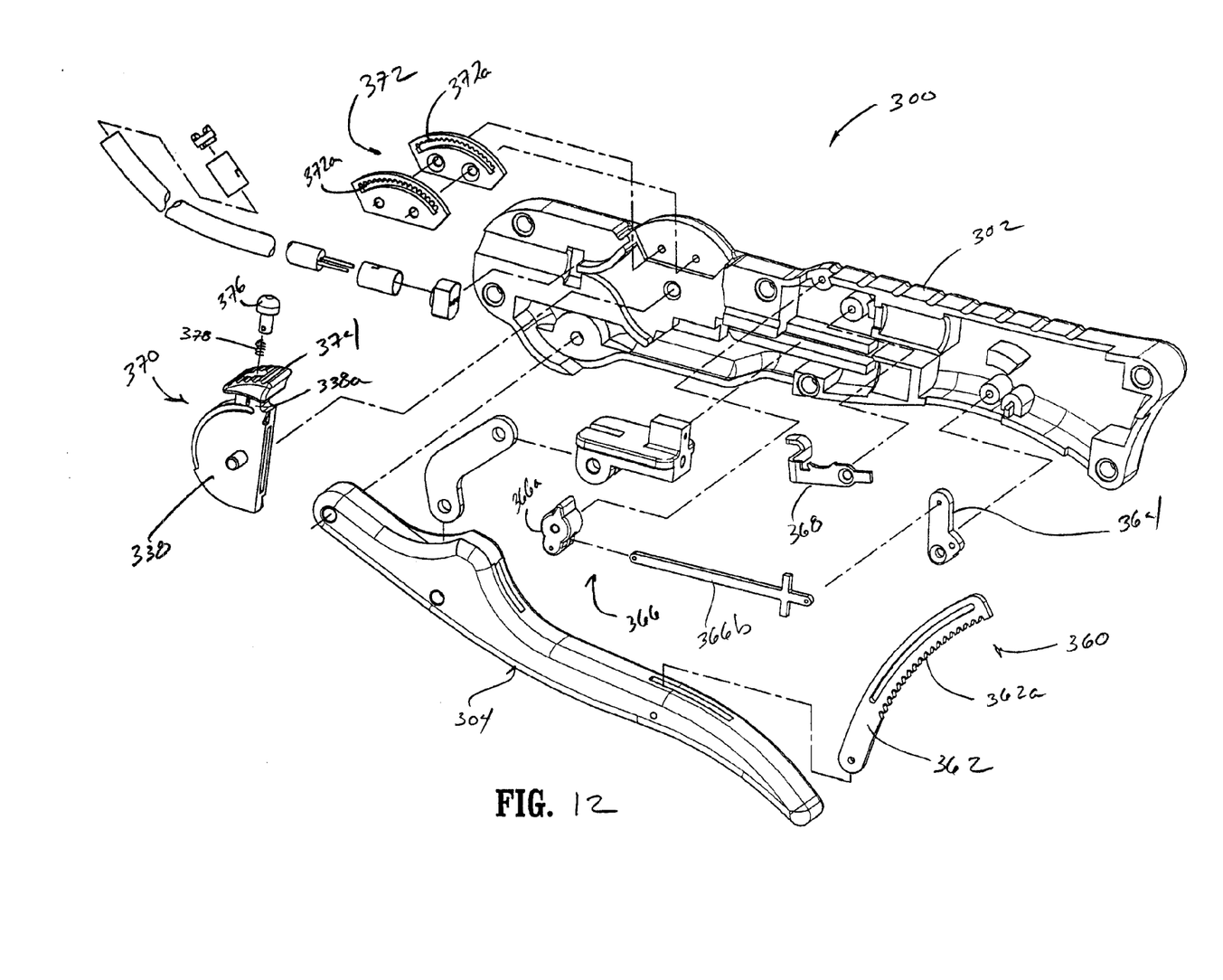
FIG. 12 is an exploded perspective view of the handle assembly of FIG. 11.
Figure 13:
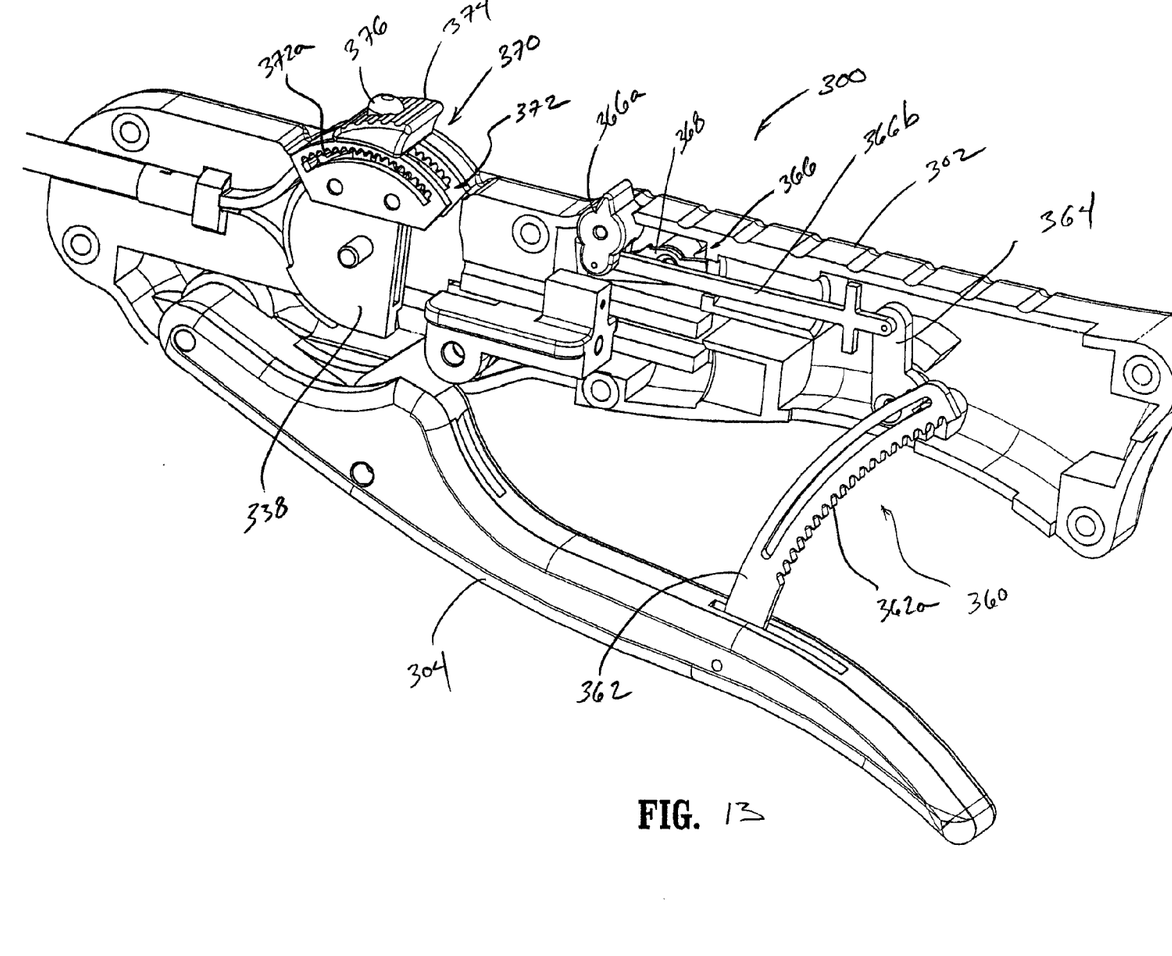
FIG. 13 is a perspective view of the handle assembly of FIGS. 11 and 12, illustrated with a housing half-section removed therefrom.
Figure 14:
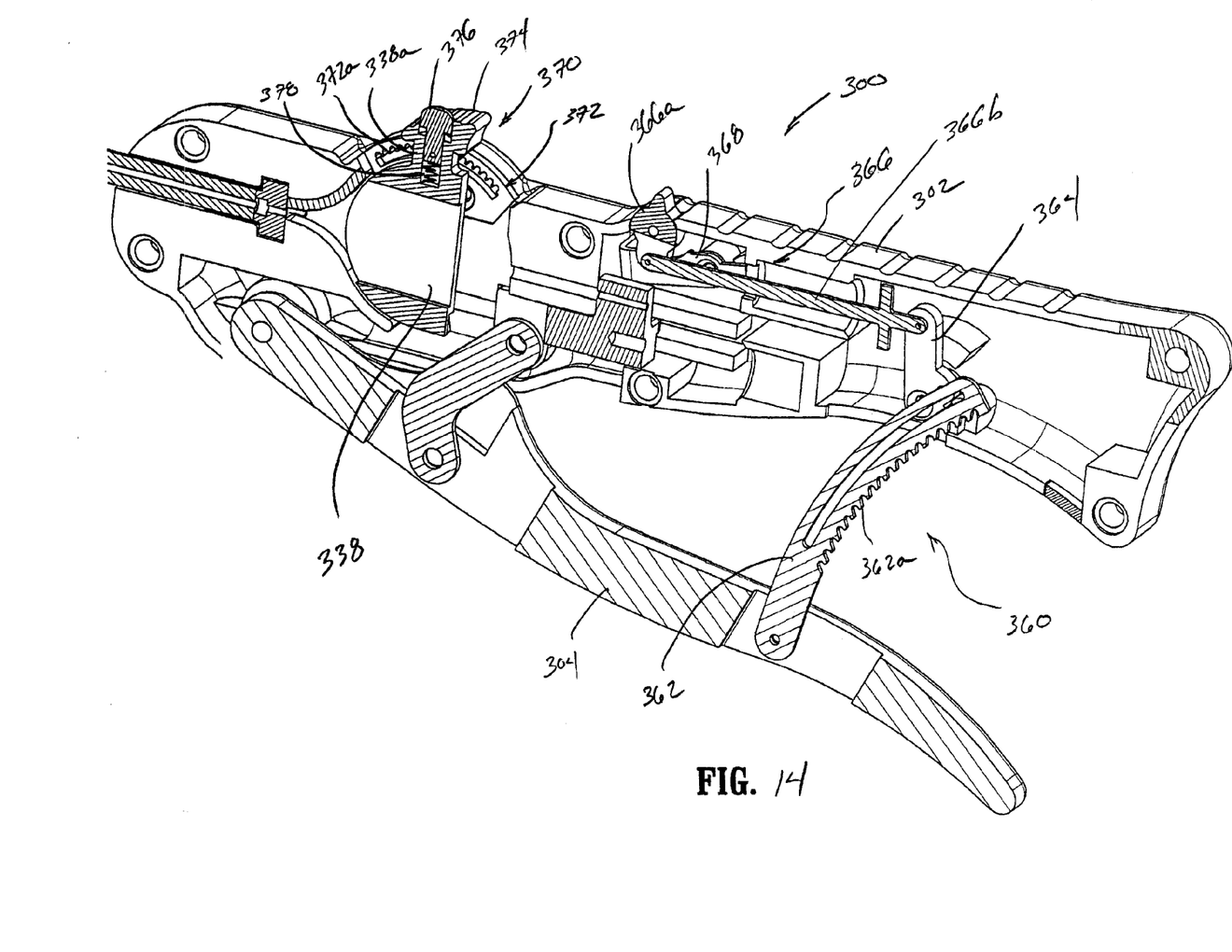
FIG. 14 is a longitudinal, cross-sectional view of the handle assembly of FIGS. 11-13.

Turning now to FIGS. 8-10, an end effector for use with handle assembly 100 is generally designated as 200. End effector 200 may be in the form of a surgical grasper, a surgical shear or any other useful surgical device. End effector 200 is adapted to be particularly useful in endoscopic or laparoscopic procedures wherein end effector 200, is insertable into an operative site, via a cannula assembly or the like (not shown).

As seen in FIGS. 8-10, end effector 200 of the stitching device is supportable on or extends from a handle assembly 100 (see FIGS. 1-7) and/or a distal end of an elongate tubular body portion (not shown) extending distally from handle assembly 100 and defining a longitudinal axis and a lumen therethrough. End effector 200 may be operatively associated with or supported on a distal end of elongate body portion and may be remotely operable by handle assembly 100.

End effector 200 includes a neck assembly 210 supported on a distal end of a shaft extending from handle assembly 100 or extending directly from handle assembly 100, and a tool assembly 220 supported on a distal end of neck assembly 210. Neck assembly 210 includes a plurality of joints 212 each including a distal knuckle 212*a* and a proximal clevis 212*b* formed therewith. Each knuckle 212*a* operatively engages a clevis 212*b* of an adjacent joint 212. Each joint 212 defines a central lumen 212*c* formed therein and a pair of opposed lumens 212*d*, 212*e* formed on either side of central lumen 212*c*. The pair of articulation cables 140*a*, 140*b* slidably extend through respective lumens 212*d*, 212*e* of joints 212. Operation of neck assembly 210 to articulate end effector 200 thereabout, will be discussed in greater detail below.

As seen in FIGS. 8-10, tool assembly 220 of end effector 200 includes a jaw support member 222, and a pair of jaws 230, 232 mounted for pivotable movement on jaw support member 222. Jaw support member 222 defines a lumen (not shown) in a proximal end thereof and a pair of spaced apart arms 226 in a distal end thereof. A knuckle 212*a* of a distal-most joint 212 is engaged or coupled to the proximal end of jaw support member 222.

Jaws 230, 232 are pivotably mounted on support member 222 by means of a jaw pivot pin 234 which extends through holes (not shown) formed in arms 226 of support member 222 and respective pivot holes (not shown) formed in jaws 230, 232. To move jaws 230, 232 between an open position and a closed position there is provided an axially or longitudinally movable center rod or shaft 236 having a camming pin (not shown) mounted at a distal end thereof. The camming pin rides in and engages angled camming slots 230*c*, 232*c* formed in respective jaws 230, 232 such that axial or longitudinal movement of the center rod causes jaws 230, 232 to be cammed between open and closed positions.

Each jaw 230, 232 defines a respective tissue engaging surface 230*a*, 232*a*. As seen in FIG. 8, each tissue engaging surface 230*a*, 232*a* of jaws 230, 232 is provided with teeth formed thereon or other suitable tissue grip-enhancing feature or the like.

Turning now to FIGS. 11-14, a handle assembly for operating, manipulating and/or controlling endoscopic and/or endoluminal devices and/or instruments, in accordance with another embodiment of the present disclosure, is generally designated as 300. Handle assembly 300 is substantially similar to handle assembly 100 and thus will only be discussed in further detail herein to the extent necessary to identify differences in construction and operation thereof.

As seen in FIGS. 11-14, handle assembly 300 includes a ratchet mechanism 360 operatively associated with trigger 304. Ratchet mechanism 360 includes a ratchet rack 362 having a first end pivotally connected to trigger 304 and a second end slidably extending into housing 302. Ratchet mechanism 360 further includes a pawl 364 supported in housing 302 and operatively engaged with ratchet rack 362. In use, as trigger 304 is squeezed, pawl 364 engages with teeth 362*a* of ratchet rack 362 to thereby maintain the location and/or position of ratchet rack 362 and trigger 304 relative to housing 302. In this manner, the jaws (not shown) of the device may be maintained in a partially or fully closed position without the operator having to physically hold trigger 304 in a partially or fully actuated position.

Ratchet mechanism 360 may be provided with a release assembly 366 supported on housing 302 of handle assembly 300. Release assembly 366 may include a release button 366*a* supported on housing 302 and a release lever 366*b* interconnecting release button 366*a* and pawl 364. Release mechanism 366 is biased, by a suitable biasing member 368, to a position where pawl 364 is maintained in engagement with ratchet rack 362. In use, in order to release pawl 362 from engagement with teeth 362*a* of ratchet rack 362, release button 366*a* is actuated thereby moving release lever 366*b* to disengage pawl 364 from ratchet rack 362.

As seen in FIGS. 11-14, handle assembly 300 further includes a ratchet mechanism 370 operatively associated with articulating member 338 of articulation assembly 330. Ratchet mechanism 370 includes a ratchet rack 372 supported on housing 302 and operatively associated with articulating member 338. Handle assembly 300 further includes an articulation trigger 374 supported on the end of an arm 338*a* extending from articulating member 338 and supporting a pawl 376 of ratchet mechanism 370. Pawl 376 of ratchet mechanism 370 is operatively engaged with teeth 372*a* of ratchet rack 372. Pawl 376 may be biased, by a suitable biasing member 378, to a position which is in engagement with teeth 372*a* of ratchet rack 372.

In use, pawl 376 is depressed in order to move actuation trigger 374. As articulation trigger 374 is translated relative to ratchet rack 372 and housing 302, to actuate articulating member 338, pawl 376 may be released to re-engage teeth 372a of ratchet rack 372 to thereby maintain the location and/or position of articulating member 338 relative to housing 302. In this manner, the articulation of the jaws (not shown) of the device may be maintained in a partially or fully articulated position without the operator having to physically hold articulation trigger 374 in a partially or fully actuated position.

Ratchet mechanism 370 may be freely moveably upon actuation by the user, however, ratchet mechanism 370 is configured such that upon release thereof by the user, ratchet mechanism 370 maintains the position of articulation trigger 374. Articulation trigger 374 may be incrementally movable along a length of ratchet rack 372.

While the disclosure has been particularly shown and described with reference to particular embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. An endoscopic surgical instrument, comprising:
   handle assembly for operating the surgical instrument, the handle assembly including:
      a housing;
      a trigger operatively supported on the housing;
      at least one actuation shaft operatively connected to the trigger and extending from the housing, wherein an actuation of the trigger imparts axial translation to the actuation shaft;
      at least one articulation cable operable from the housing, each articulation cable including a distal end operatively connectable with an end effector; and
      an articulation control element slidably movable on the housing, the articulation control element operatively interposed between and engaging a first ratchet rack and a second ratchet rack, wherein the first ratchet rack and the second ratchet rack are configured to selectively maintain a position of the articulation control element relative to the housing;
   an articulatable neck assembly supported on and extending from the handle assembly, wherein each actuation shaft and articulation cable extends through the neck assembly; and
   an end effector operatively supported on the neck assembly, the end effector including a pair of pivotably mounted, juxtaposed jaws, wherein the jaws are movable at least between an open position and a closed position, and wherein a distal end of the at least one actuation shaft is operatively engaged with the pair of jaws to effectuate opening and closing of the jaws, wherein a sliding movement of the articulation control element results in articulation of the articulatable neck assembly.

2. The endoscopic surgical instrument according to claim 1, wherein movement of the articulation control element results in movement of the at least one articulation cable to effectuate an articulation of the neck assembly.

3. The endoscopic surgical instrument according to claim 1, wherein movement of the at least one articulation cable in a first direction causes an articulation of the end effector in a first direction and movement of the at least one articulation cable in a second direction results in articulation of the end effector in a second direction.

4. The endoscopic surgical instrument according to claim 2, further comprising a pair of articulation cables each having a proximal end operatively connected to the articulation control element such that movement of the articulation control element in a first direction results in movement of a first articulation cable in a first direction and movement of a second articulation cable in a second direction; and movement of the articulation control element in a second direction results in movement of the first articulation cable in the second direction and movement of the second articulation cable in the first direction.

5. The endoscopic surgical instrument according to claim 1, wherein the trigger imparts proximal axial movement to the actuation shaft when the trigger is squeezed to close the jaws, and distal axial movement to the actuation shaft when the trigger is released to open the jaws.

6. The endoscopic surgical instrument according to claim 1, wherein the handle assembly further comprises a second ratchet mechanism operatively associated with the trigger, wherein the ratchet mechanism is configured to selectively maintain the position of the trigger relative to the housing and thus the relative open or closed position of the jaws.

7. The endoscopic according to claim 6, wherein the housing assembly further includes a release assembly operatively associated with the second ratchet mechanism, wherein the release assembly is configured such that actuation of the release assembly results in a disengagement of the second ratchet mechanism.

8. The endoscopic surgical instrument according to claim 7, wherein the second ratchet mechanism includes a ratchet rack having a first end coupled to the trigger and a second end extending into the handle, and a pawl selectively operatively engageable with teeth of the ratchet rack of the second ratchet mechanism.

9. The endoscopic surgical instrument according to claim 8, wherein the release assembly includes a release button supported on the housing, and a release lever interconnecting the release button and the pawl, wherein actuation of the release button selectively engages and disengages the pawl and the ratchet rack of the second ratchet mechanism.

10. The endoscopic surgical instrument according to claim 8, wherein the pawl is biased into engagement with the ratchet rack of the second ratchet mechanism.

11. The endoscopic surgical instrument according to claim 1, wherein the articulation control element includes an articulation trigger.

12. The endoscopic surgical instrument according to claim 11, wherein the articulation trigger is incrementally movable along the first ratchet rack and the second ratchet rack.

13. The endoscopic surgical instrument according to claim 1, wherein the pair of jaws define a surgical grasper.

* * * * *